(12) United States Patent
Knudsen et al.

(10) Patent No.: US 10,369,057 B2
(45) Date of Patent: Aug. 6, 2019

(54) INTEGRATED WIRELESS EARBUDS AND EARPLUGS

(71) Applicant: Innate Devices, LLC, Mapleton, UT (US)

(72) Inventors: Tyler Knudsen, Spanish Fork, UT (US); Shaun Knudsen, Mapleton, UT (US)

(73) Assignee: Innate Devices, LLC, Mapleton, UT (US)

( * ) Notice: Subject to any disclaimer, the term of this patent is extended or adjusted under 35 U.S.C. 154(b) by 0 days.

(21) Appl. No.: 15/472,131

(22) Filed: Mar. 28, 2017

(65) Prior Publication Data

US 2017/0319392 A1    Nov. 9, 2017

Related U.S. Application Data

(60) Provisional application No. 62/314,217, filed on Mar. 28, 2016.

(51) Int. Cl.
| | |
|---|---|
| *A61F 11/08* | (2006.01) |
| *H04R 5/033* | (2006.01) |
| *H04R 1/10* | (2006.01) |

(52) U.S. Cl.
CPC ............ *A61F 11/08* (2013.01); *H04R 1/1016* (2013.01); *H04R 1/1058* (2013.01); *H04R 1/1083* (2013.01); *H04R 5/033* (2013.01); *A61F 2011/085* (2013.01); *H04R 1/1025* (2013.01); *H04R 2201/103* (2013.01); *H04R 2420/07* (2013.01)

(58) Field of Classification Search
None
See application file for complete search history.

(56) References Cited

U.S. PATENT DOCUMENTS

| | | | |
|---|---|---|---|
| 6,006,857 A * | 12/1999 | Leight | A61F 11/08 128/864 |
| 9,706,283 B2 * | 7/2017 | Stoch | H04R 1/1016 |
| 2002/0025055 A1 | 2/2002 | Stonikas et al. | |
| 2010/0098285 A1 | 4/2010 | Kusuda et al. | |

(Continued)

OTHER PUBLICATIONS

International Search Report and Written Opinion from PCT International Application No. PCT/US2017/024619, dated Aug. 14, 2017, 10 pages.

*Primary Examiner* — Paul W Huber
(74) *Attorney, Agent, or Firm* — Durham Jones & Pinegar, P.C., Intellectual Property Law Group

(57) ABSTRACT

A wireless audio system suppresses exterior noise and directs desired sound into a user's ear canal. An audio system may include an earplug to create a seal in the interior of an ear canal. The earplug may include a ribbed exterior profile and can be flexible to create the seal. A speaker may be inserted within the earplug. A channel may extend through a body of the earplug to direct sound into a user's ear canal. A proximal opening may extend from the speaker to the channel of the earplug, and an audio wire may be connected to the speaker. The audio wire may connect to a wireless receiver, or other receiver, to allow audio data to pass through the wire and to the speaker, where it can be converted to audio that is passed directly into the ear canal of the user.

18 Claims, 6 Drawing Sheets

(56) References Cited

U.S. PATENT DOCUMENTS

| | | | |
|---|---|---|---|
| 2010/0195860 A1* | 8/2010 | Becker | H04R 1/1016 381/371 |
| 2014/0112520 A1* | 4/2014 | Knudsen | H04R 1/1083 381/380 |
| 2015/0146880 A1* | 5/2015 | Boni | H04R 1/1008 381/74 |
| 2017/0070801 A1* | 3/2017 | Nguyen | H04R 1/105 |
| 2017/0094386 A1* | 3/2017 | Trainer | H04R 1/1016 |
| 2017/0188133 A1* | 6/2017 | Olson | H04R 1/1066 |

* cited by examiner

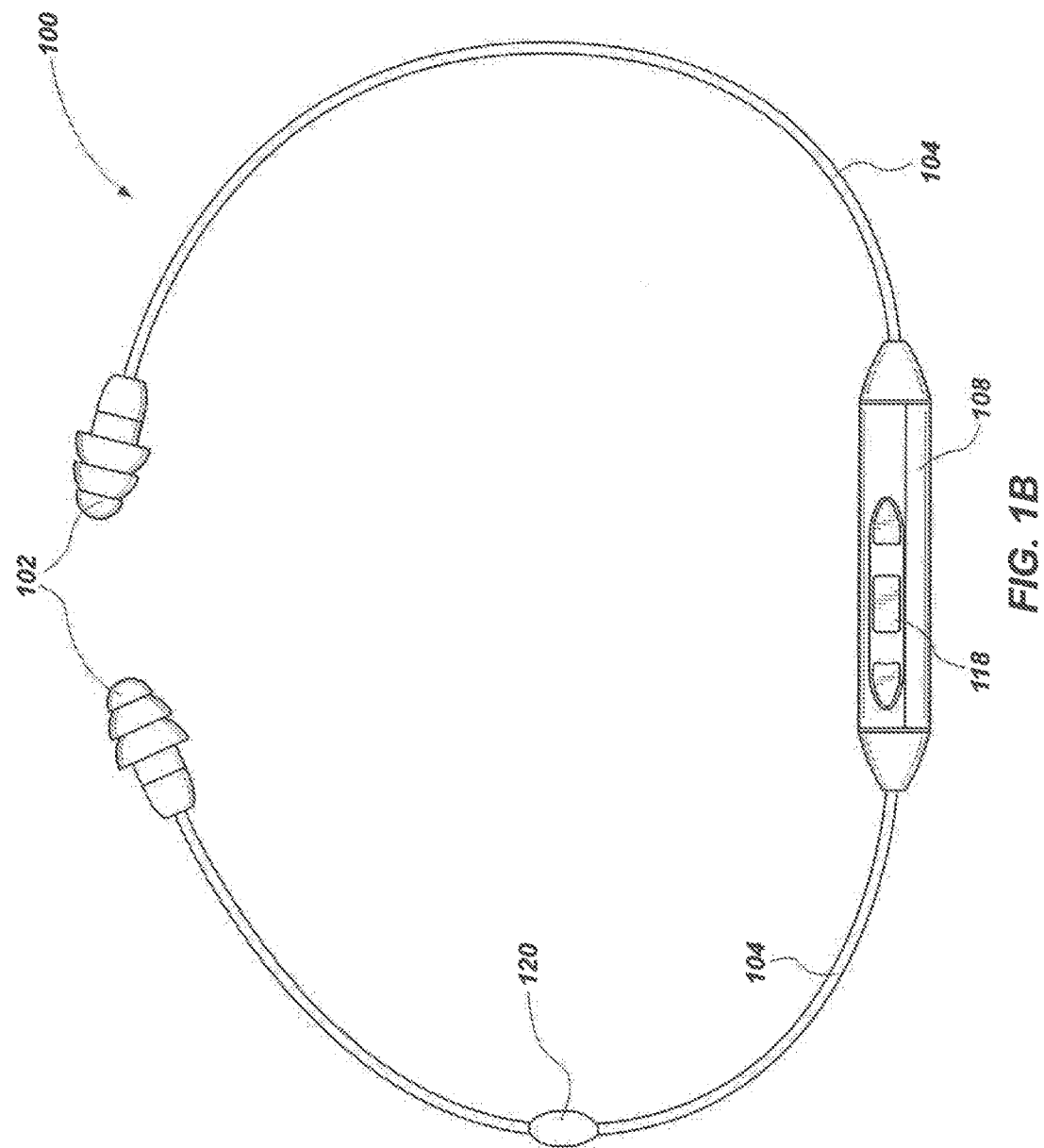

INTEGRATED WIRELESS EARBUDS AND EARPLUGS

CROSS-REFERENCE TO RELATED APPLICATIONS

This application claims the benefit of priority to the U.S. Provisional Patent Application No. 62/314,217 entitled "INTEGRATED WIRELESS EARBUDS AND EARPLUGS" and filed Mar. 28, 2016, and is incorporated herein by reference in its entirety. In addition the following applications are incorporated by reference in their entirety, U.S. Patent Application Ser. No. 61/715,754 filed on Oct. 18, 2012 and titled "AUDIO LISTENING DEVICE," and U.S. patent application Ser. No. 14/056,494 filed on Oct. 17, 2013 and titled "INTEGRATED EARBUDS AND EARPLUGS AND METHODS AND SYSTEMS AND KITS ASSOCIATED THEREWITH."

TECHNICAL FIELD

The present disclosure generally relates to audio output devices. More particularly, aspects of the present disclosure relate to audio output devices that also substantially block outside noise and may be considered wireless with respect to being wired to the listening device such as an MP3 player or other audio/visual device or audio device (hereinafter "audio device") via Bluetooth® or wired access. More particularly still, aspects of the present disclosure relate generally to ear plugs configured to restrict external sound from being heard, but which also act as an earbud providing specific external sounds directly into the ear canal while not requiring that the earbuds to be wired into the audio device.

BACKGROUND

Noise, while being an irritation, is also a cause of hearing loss when the ears are either subjected to a single loud noise or are repeatedly subjected to levels of noise above a safe level. Such noise is increasingly becoming an issue in industrial and other workplace settings where machinery operates. While some efforts may be made to reduce noise produced by machinery, the exposure to high levels of noise, or even repeated exposure to lower levels of noise, may lead to hearing loss.

For instance, the Occupational Safety and Health Administration ("OSHA") within the United States Department of Labor has recognized that prolonged or even short exposure to some sound levels may lead to permanent hearing loss. Consequently, OSHA has set forth regulations requiring employers to develop and implement a hearing conservation program whenever exposure over an eight hour period averages 85 decibels or greater. An employer may even be required to provide protective equipment in some cases. By way of example, if an employee is subjected to sound exceeding an average of 90 decibels within an eight hour period, or sound exceeding an average of 115 decibels for fifteen minutes or less, the employer may be required to provide protective equipment. For sound levels between 90 and 115, different exposure periods may result in requirements for employer-provided ear protection.

Ear protection has traditionally taken the form of earplugs, semi-insert ear plugs, or ear muffs. Ear plugs may be pre-molded or moldable, and can be inserted in the ear to block the ear canal. Semi-insert ear plugs can include ear plugs held over the ends of the ear canal by a rigid headband. Ear muffs may include a pair of sound-attenuating ear cushions attached to hard outer cups. The ear cushions fit around the ear and the hard outer cups are connected by a head band.

Each type of ear protection may be effective in attenuating some noise, whether the noise originates at a workplace, at home (e.g., while vacuuming, in the workshop, etc.), at a sporting event (e.g., motor sports), during travel (e.g., on an airplane ride), or at other locations. The effectiveness of such devices also can provide certain drawbacks. For instance, when an earplug is in a person's ear, the person may not be able to hear music playing on the radio, hear announcements at a motorsports race, or the like. While a person could instead use an earbud connected to a radio or media player, earbuds have not traditionally been designed to prevent hearing loss. Earbuds may therefore not sufficiently attenuate external noise, thereby allowing ear damage. Headphones that do attenuate external noise (e.g., noise cancelling headphones) are traditionally large and oversized, and therefore lack discreteness, or may be easily damaged in small spaces.

SUMMARY

In accordance with aspects of the present disclosure and embodiments are described or would be understood and which relate to audio output systems that also protect against hearing loss. An example audio system suppresses exterior noise and directs desired sound into a user's ear canal. The audio system may include an earplug to create a seal in the interior of an ear canal. The earplug assembly may include the earplug, a speaker driver, and a first speaker housing which may be proximal a second speaker housing which may be distal the first speaker housing. The second speaker housing may include a tubular post extending distally and which may engage the earplug, a "stem." The first and second speaker housings may be integrated or may be separate pieces welded together. One embodiment of the earplug may include a ribbed exterior profile and can be flexible to create the seal. An alternate embodiment earplug may include a silicone center, which may be rigid, with pliable or deformable foam surrounding the silicone center. The pliable foam may conform to the interior of an ear canal. To also act as an earbud, the earplug can include a speaker driver therein. The speaker driver may be in communication with a distal opening extending from the speaker driver toward the distal end of the earplug. Sound from the speaker driver may pass through the distal opening into the user's ear canal. A proximal opening may extend from the speaker driver to the proximal end of the earplug, and can receive an audio wire connected to the speaker driver. The audio wire may connect to a wireless receiver which receives a wireless signal from an audio device to allow audio data to pass through the wireless receiver through the wire and to the speaker, where it can be converted to audio that is passed directly into the ear canal of the user.

Other aspects, as well as the features and advantages of various aspects, of the present disclosure will become apparent to those of ordinary skill in the art through consideration of the ensuing description, the accompanying drawings and the appended claims.

BRIEF DESCRIPTION OF THE DRAWINGS

In the drawings:

FIG. 1b illustrates an alternate view of the plugfone device of FIG. 1a with buttons on the audio receiver;

FIG. 2b illustrates a second perspective view of the earplug of FIG. 2a;

FIG. 2c illustrates a distal view of the earplug of FIG. 2a;

FIG. 2d illustrates a proximal view of the earplug of FIG. 2a;

FIG. 2e illustrates a side view of the earplug of FIG. 2a;

FIG. 3b illustrates a second perspective view of the earplug of FIG. 3a;

FIG. 3c illustrates a proximal view of the earplug of FIG. 3a;

FIG. 3d illustrates a side view of the earplug of FIG. 3a;

FIG. 3e illustrates a cross-sectional side view of the earplug of FIG. 3a;

FIG. 4b illustrates a second perspective view of the speaker housing of FIG. 4a;

FIG. 4c illustrates a side view of the speaker housing of FIG. 4a;

FIG. 4d illustrates a proximal view of the speaker housing of FIG. 4a;

FIG. 4e illustrates a cross-sectional side view of the speaker housing of FIG. 4a;

FIG. 5a illustrates a first perspective view of the audio receiver of the device of FIG. 1a;

FIG. 5b illustrates a second perspective view of the audio receiver of the device of FIG. 5a;

FIG. 5c illustrates a side view of the audio receiver of FIG. 5a; and

FIG. 5d illustrates an alternate side view of the audio receiver of FIG. 5a.

DETAILED DESCRIPTION

Example embodiments of the present disclosure are directed to devices and systems, for attenuating sound from external sources while also delivering desired audio directly to an ear canal of a user. More particularly, example embodiments of the present disclosure are directed to systems and devices that include an earplug effective in preventing or minimizing hearing loss, while also including an earplug assembly, which may include a speaker and speaker assembly, allowing the user to effectively hear desired audio. By being able to block unwanted background noise while continuing to hear desired audio, a user may have a more enjoyable shift at work, enjoy household chores while reducing risks of hearing loss, or reduce noise from fans or cars at the track while also listening in on a favorite driver's radio. Embodiments of the present disclosure may include countless other uses including, but not limited to, use at home, school, vacation, work, or the like.

Figure 1A:
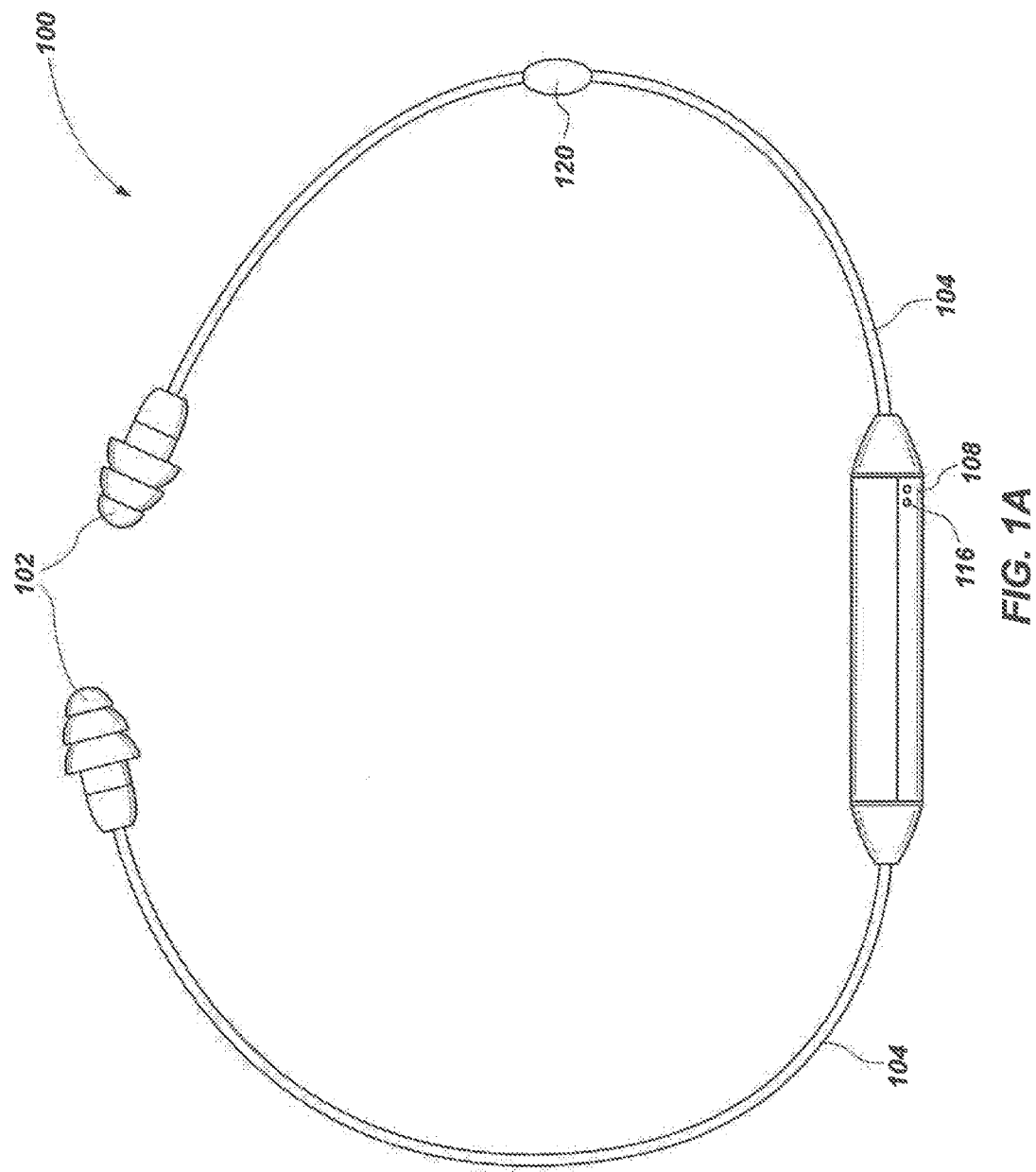
FIG. 1a illustrates a perspective view of an earplug and earbud device (defined later herein as "plugfone") with a wireless audio receiver, earplugs, and housed speakers.
Figure 2A:
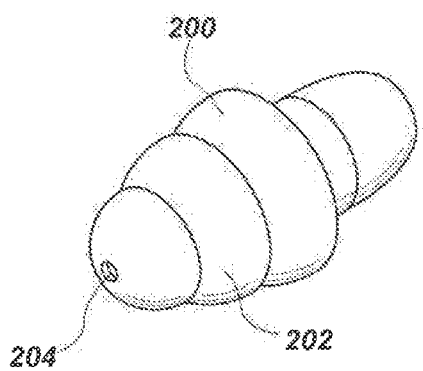
FIG. 2a illustrates a first perspective view of a first embodiment of an earplug of FIG. 1a with a sound canal.
Figure 2B:
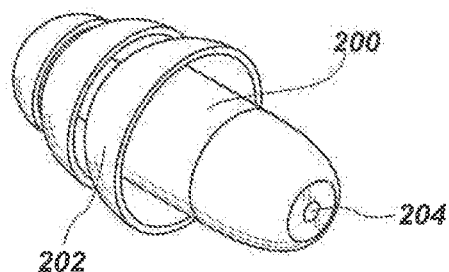
Figure 2C:
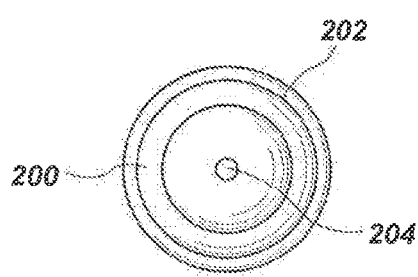
Figure 2D:
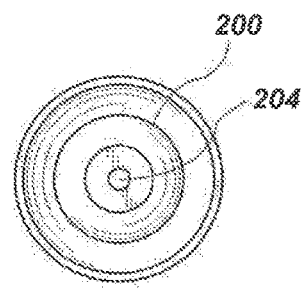
Figure 2E:
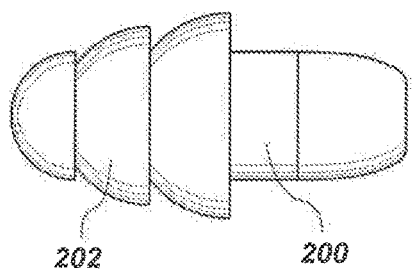
Figure 3A:
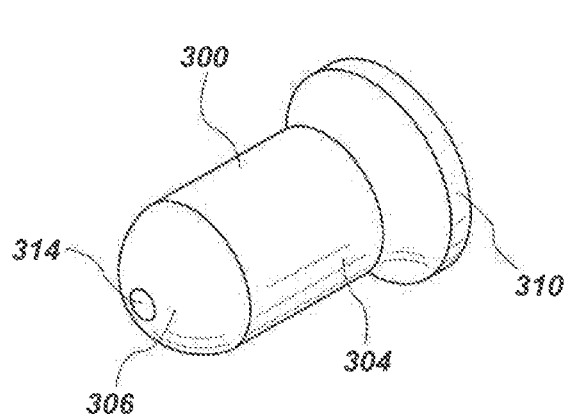
FIG. 3a illustrates a first perspective view of a second embodiment of an earplug with a sound canal.
Figure 3B:
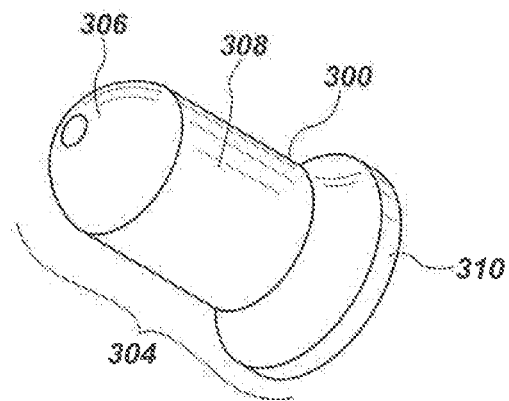
Figure 3C:
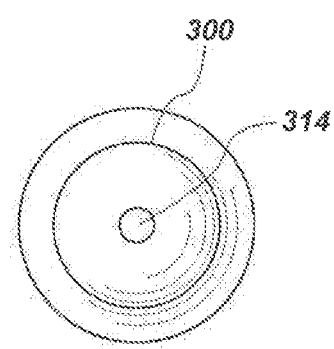
Figure 3D:
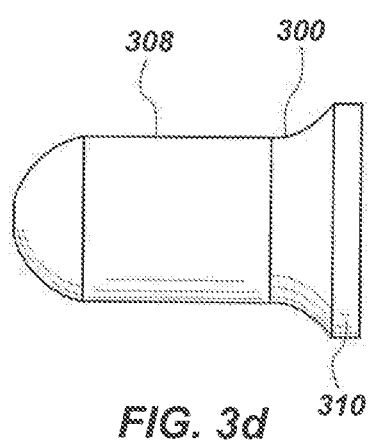
Figure 3E:
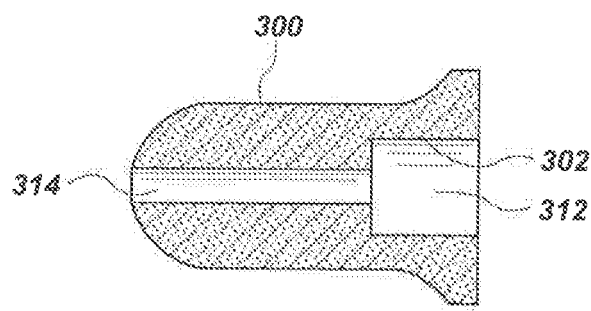
Figure 4A:
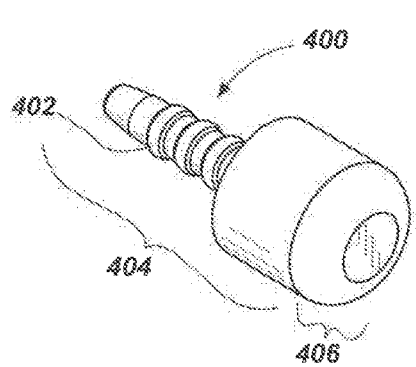
FIG. 4a illustrates a first perspective view of a speaker housing.
Figure 4B:
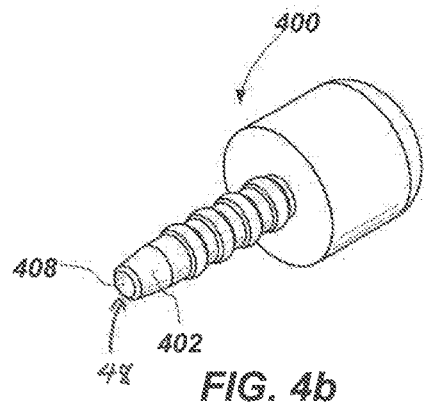
Figure 4C:
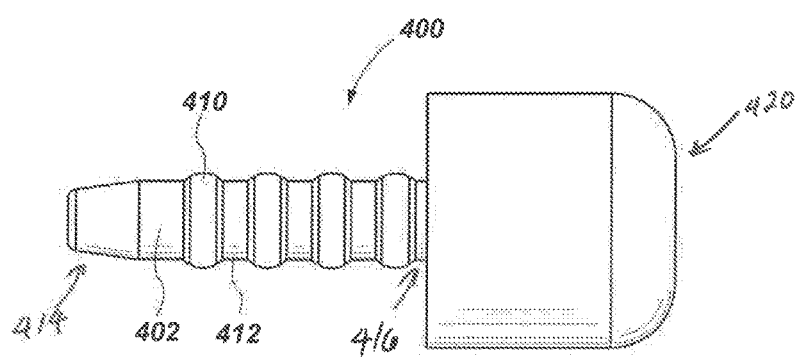
Figure 4D:
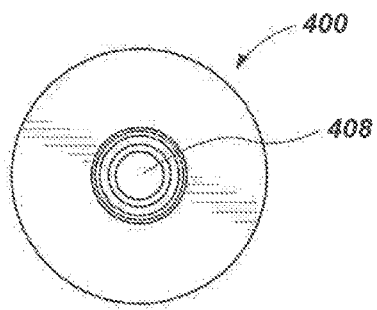
Figure 4E:
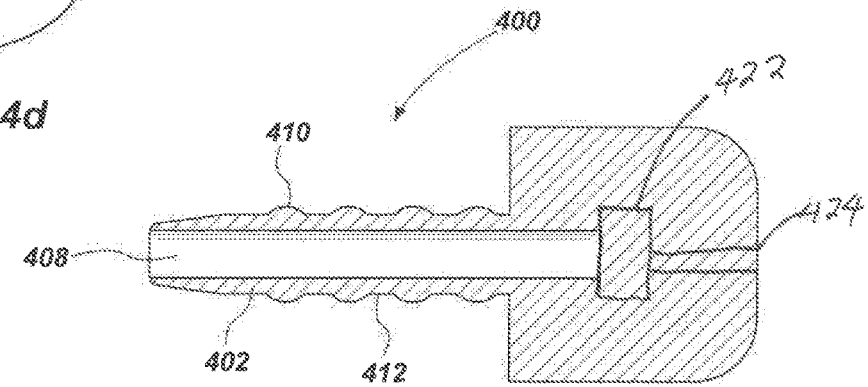
Figure 5A:
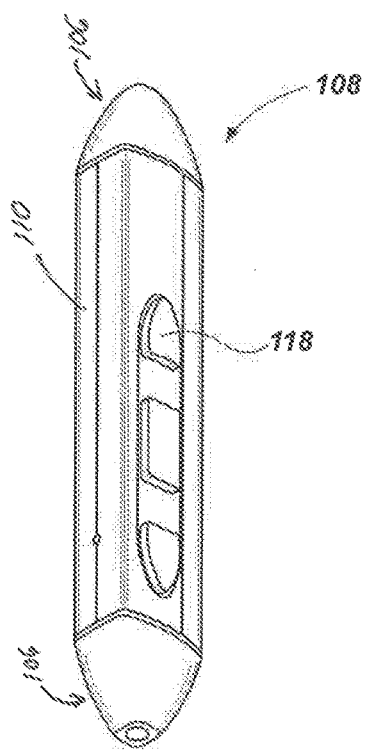
Figure 5B:
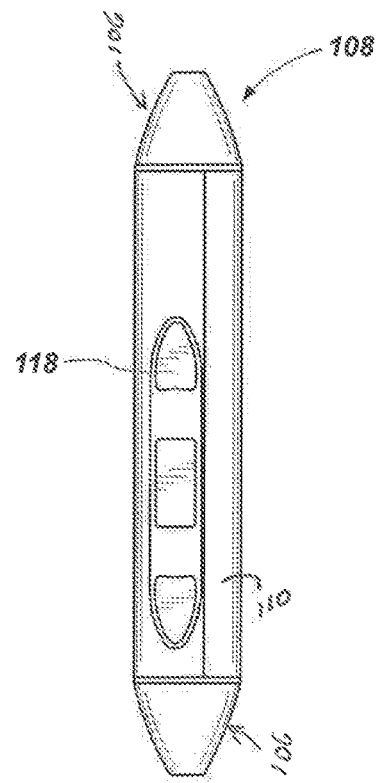
Figure 5C:
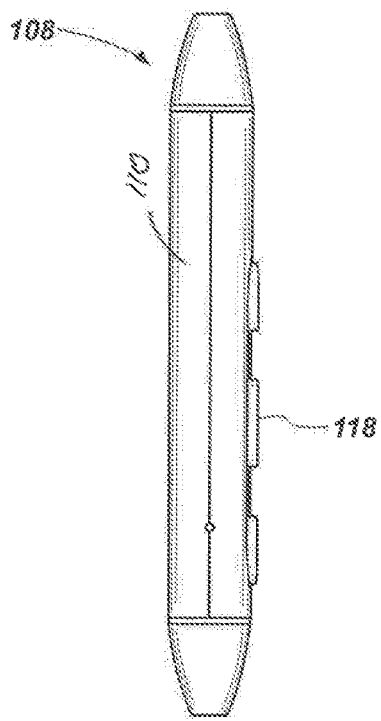
Figure 5D:
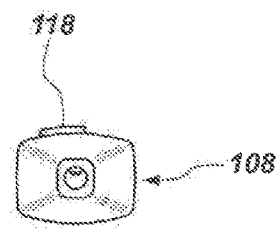

Referring to FIGS. 1a and 1b, one embodiment of the present disclosure relates to an audio system 100 combining the benefits of an earplug with those of an earbud while also providing a user the ability to listen wirelessly. In particular, an earplug may attenuate sound from external sources. As an example, an earbud may be tested and rated to determine its noise reduction rating. Example noise reduction ratings may decrease sound levels by twenty-five decibels or more to provide a benefit of hearing loss prevention. While an earplug may be designed primarily to reduce or attenuate sound, an earbud, in contrast, may be primarily designed to allow sound. As an example, an earbud may be connected to a portable media player or other audio source. Sound from the audio source may be provided by a speaker in the earbud. If the earbud is then in the user's ear, the audio may be played by the speaker and directly into the ear canal.

When combined as described herein, example embodiments may therefore provide sound attenuation aspects of an earplug, while also providing audio output capabilities of an earbud or headphone. Example embodiments providing such dual features may be referred to herein as "plugfone(s)." In particular, plugfones may include ear plugs that are also an earbud. Plugfones may offer the same level of hearing protection expected from an earplug or other sound suppressing devices, yet can allow the user to listen to music, audio books, radio, podcasts, television, movies or other audio sounds or other selected sounds at a comfortable and safe level while in a noise filled environment. Plugfones may be used in a variety of settings where the user prefers or is mandated to wear hearing protection, yet would also like the convenience or luxury of listening to audio without the worry of a wire plugged into an audio device.

In the particular embodiment shown in FIG. 1a-1b, the audio system 100 may include a set of plugfones 102. Each plugfone 102 may be configured to be placed within the ear of a user. The particular structure or configuration of the plugfones 102 may vary. In FIG. 1a-1b, for instance, the plugfones 102 are shown as having a tapered external profile. The distal end may be narrow so as to fit within the ear canal of the user, and may then expand outward toward the proximal end. Such a profile may allow for simplified insertion and securement of the plugfones 102 within the ear canal. Optionally, the tapered profile may also, or alternatively, be flanged or ribbed. Such flanges or ribs may be flexible, and can potentially flex and create a seal within the ear canal to attenuate external noise (see FIG. 2).

The example configuration of the plugfones 102 in FIG. 1a-1b is merely illustrative, and other configurations are contemplated. For instance, the plugfones 102 may have other profile shapes, including cylindrical, bullet-shaped, or the like. In other embodiments, the plugfones 102 may be formed of a variety of different materials (e.g., foam, memory foam, silicone, wax, thermoplastics, etc.)

The audio system 100 of FIG. 1a-1b also illustrates that the plugfones 102 may each be connected to an audio input, which may be a receiver 108, which may be a wireless receiver or an audio receiver or Bluetooth® receiver. In this particular embodiment, an audio wire 104 is connected to each plugfone 102 from the wireless receiver 108. The audio wire 104 may generally be any wire capable of carrying acoustic, electronic, or other signals capable of being interpreted as sound. In this embodiment, a speaker may be located within the plugfones 102 and also connected to the wire 104 to convert a signal into a sound that is audible to the human ear.

At least in the first embodiment, the audio wires 104 may be separate, while in other embodiments the audio wires 104 may be at least partially combined. In FIG. 1a-1b, for instance, the wireless receiver 108 may be positioned at a medial portion of the audio system 100 wherein the audio wires 104 from each plugfone 102 intersect at the wireless receiver 108. The audio wires 104 may each connect to the wireless receiver 108 and extend therefrom toward the plugfones 102. In a wired embodiment a junction may be positioned at a medial portion of the audio system 100. At a lower portion of the junction, there may be a single audio wire 104 extending from the junction to the audio system 100. The single audio wire 104 may effectively combine the audio sent through each of the audio wires 104.

Alternatively the receiver 108 may be positioned toward or biased toward one of the plugfones 102 wherein the receiver 108 may be closer to one plugfone 102 versus the other plugfone 102. In this instance one audio wire 104 to one plugfone 102 may be longer than the other audio wire 104 to the other plugfone 102. In a single plugfone 102 (one earplug one speaker) embodiment the receiver 108 may be incorporated into the one plugfone 102 itself.

While the junction and/or the wireless receiver 108 may be described as joining the audio wires 104, it may also be described as a splitter. For instance, the combined audio wire 104 may split within the wireless receiver 108, thus, in some embodiments, each audio wire 104 provides the same audio to a respective plugfone 102. In other embodiments, such as in the case of stereo sound, different audio signals, or channels, may be provided to each audio wire 104, and thus, to each plugfone 102.

While the junction may split the sound conveyed using the combined audio wire 104, in other embodiments, different components may split the sound and/or the audio wires 104. For instance, the combined audio wire 104 may physically connect to electronically separate audio wires 104. The audio input may, however, provide two different connections and thereby separate audio provided by the audio system 100.

In a wired embodiment, the audio input may include an audio jack. For instance, a 3.5 mm jack may be used and inserted into a corresponding jack on the audio system 100. The audio system 100 may itself have any number of configurations or uses. In some embodiments, the audio system 100 may include a personal media player, smart phone, radio, computer, television, tablet or the like.

In general, the collective length of the audio wires 104 may be sufficient to allow comfortable use of the plugfones 102 with the audio system 100. Such length may thus vary based on any number of conditions or considerations. In at least some embodiments, the collective length of the audio wires 104, may be within 0.25 meter to about 3 meters, although the length may be larger or smaller in other embodiments, with 0.5 meter being a good medium. In a more particular embodiment, the length may be between about 1 meter and about 2 meters.

Referring to FIGS. 5a-5d and 1a-1b, the receiver 108 may include a body 110 with a substantially rectangular shape. Alternatively, the body 110 may be any polygonal, spherical, oval, or other shape. The body 110 may include tapered ends 106 where the audio wires 104 exit the receiver 108. The body 110 may include a charging port 116, which may include at least one electrical contact that can engage a charging device. On an opposite side of the body 110 from the charging port 116, the wireless receiver 108 may include buttons 118 or switches for a user to interface with that will engage the wireless receiver 108 to the audio system 100. The buttons 118 may transmit a signal from the wireless receiver 108 to the audio system 100 and may perform functions such as increasing or decreasing volume; turning the audio system 100 on and off; turning the wireless receiver 108 on and off; switching songs or playlists; shuffling a playlist; advancing a track or rewinding a track; and others.

The position of the charging port 116 and the buttons 118 may vary. The charging port 116 may be on the same side or adjacent side to the buttons 118. The charging port 116 may include a snap feature, magnet feature, press-fit feature or other securing feature to engage a charging device. The buttons 118 may include haptic feedback or clickable buttons or may include a slight bending motion to input signals as previously described herein.

One of the audio wires 104 that extend from the wireless receiver 108 may include a microphone 120 embedded in the wire housing of the audio wires 104. Thus, allowing the user to utilize the audio system 100 as a wireless headset to talk on the phone. Alternatively, in a single plugfone 102 embodiment the microphone 120 may be incorporated into the receiver 108 and the plugfone 102 itself.

Referring to FIGS. 2a-e, an earplug may include a body 200 that includes a set of multiple circumferential ribs/flanges 202 and a channel 204 passing through the body 200 in a longitudinal direction. The channel 204 may include an opening on the distal end and the proximal end of the body 200 and is configured to allow sound to pass there through into the ear canal of a user from the speaker within the plugfones 102. The earplug body 200 may taper toward a distal end and each successive rib/flange 202 may increase in size (in a cross-sectional diameter) moving distally to proximally. The number of ribs/flanges 202 may vary from one to six or more; however, in the figures three ribs/flanges 202 are shown. The tapered distal end of the earplug body 200 may generally conform to the shape of the entrance of the ear canal of a user. The ribs 202 may be generally deformable. The ribs 202 may bend, flex, or otherwise conform to the shape of the users' ear canal, and may thereby create a seal within the ear canal to suppress sounds from passing through the ribs 202 and into the inner ear.

The proximal end of the earplug body 200 may include an engagement feature 206 which engages a post, or stem 402 of a speaker housing 400 (as depicted in FIGS. 4a-4e). The earplug 200 is reversibly fixed to the speaker housing 400 via the engagement feature 206 which resides within the channel 204 and may simply be a pliable substance such as rubber, silicone, plastic, and others that conforms to the stem 402 via press fit, snap fit, or other reversible engagement. The channel 204 may include grooves, barbs or ridges within the channel to more securely engage the stem 402. The force to remove the earplug body 200 from the stem 402 may be greater than the force applied when a user removes the earplug body 200 from a user's ear.

Referring to FIGS. 3a-3e, an alternate embodiment of an earplug body 300 is depicted. The earplug body 300 may include a more rigid central component or piece 302 which may be silicone, polymer, or other harder plastic to maintain its shape more so than a softer rubber. A deformable or pliable external component or piece 304 may encompass or surround the central component 302. The external component 304 may be a foam or softer polymer that conforms to the ear canal of a user when inserted into an ear canal. The earplug body 300 may be tapered toward a distal tip 306 or may be a rounded end with a conformal mid-body 308 and a wider proximal end 310 which may flare at its end. The earplug body 300 may include a void 312 within the central component 302 configured to receive the speaker housing 400 within the void 312.

The earplug body 300 may include a channel 314, similar to the previous embodiment, which passes through the center of the body 300 in a longitudinal direction. The channel 314 may have an opening at the proximal end and the distal end. The channel 314 may include an engagement feature that reversibly engages the stem 402 of the speaker housing 400 in like manner to the previous earplug body 200. The force to remove the earplug body 300 from the stem 402 may be greater than the force applied when a user removes the earplug body 300 from a user's ear.

In both embodiments, the engagement feature between the speaker housing 400 and the earplug bodies 200, 300, provide sufficient counterforce to withstand sufficient pressure to remove the earplug bodies from the ear canal of a user while not disengaging the earplug bodies 200, 300 from the speaker housing 400. The earplug bodies 200, 300 are interchangeable and sufficient force may be required to overcome the engagement features to disengage the earplugs bodies 200, 300 from the stem 402 of the speaker housing 400.

Referring to FIGS. 4a-4e, the speaker housing 400 may include a stem 402 on a first portion 404 and second portion 406 may cup the speaker 422, preventing its withdrawal from the housing 400. The second portion 406 may be separate from the first portion 404 and then welded together (e.g. glue, tape, melting, etc.) or the first and second portions 402,404 may be integrated and manufactured as a single piece. The second portion 406 may include an opening 424 to allow a wire to pass through to engage the speaker 422 and transmit electrical signals to the speaker 422 to play sound. The first portion 404 may include a housing channel 408 passing longitudinally through the body of the first portion 404, through the stem 402 of the first portion 404. An opening may be positioned at the first end 418 of the housing channel 408 to allow sound to move from the speaker 422 out of the housing 400.

Opposite the first end 418 of the housing channel 408 may be a second end 420 of the speaker housing 400 with the opening 424 allowing passage of the wire 104 to engage the speaker 422. The speaker 422 may be the same size as, larger than or smaller than the housing channel 408. The opening 424 may be sized to allow a snug passage of the wire(s) 104 through the opening 424; alternatively, the opening 424 may be sufficiently large to allow for easy passage of the wire(s) 104 through the opening 424.

The stem 402 may be tapered toward a distal end 414 or may be the same diameter as the proximal end 416 of the stem 402. The stem 402 may comprise at least one circumferential ridge 410 or groove 412 along the length of the stem 402. Multiple ridges 410 or grooves 412 may be positioned along the length of the stem 402. The ridges 410 or grooves 412 may provide frictional engagement with the earplug bodies 200, 300 when the stem 402 is inserted into the channels 204, 314 of the earplug bodies 200, 300. The ridges 410 or grooves 412 may also engage in a snap fit or complementary fit within the channels 204, 314 of the earplug bodies 200, 300. Sufficient force will be required to remove the earplug bodies 200, 300 from the stem 402 in order to disengage and alternate (or replace) the earplug bodies 200, 300.

The housing 400 may be modular and allow for replacement of different first portions 404 and second portions 406 such that replacement of a speaker 422 within the housing 400 is also possible.

The housing 400 may be formed of a more rigid thermoplastic material such as ABS or other durable polymer. Of course, other polymeric, composite, organic, metallic, or other materials may also be used. For instance, acetyl and nylon.

Those skilled in the art will therefore appreciate that the embodiments may be practiced in a variety of environments, to satisfy a number of different functions or purposes. For instance, manufacturing and industrial workers may use plugfones 102 as described herein to protect their hearing. As an example, workers in assembly lines who find themselves around loud machinery may use plugfones 102 to reduce the noise of the machinery and/or better hear music or other audio provided through the plugfones 102. Operators of heavy equipment may also use plugfones 102, as well as riders of motorcycles (e.g., for reduced road or exhaust pipe noise). Students who are looking for a quiet studying environment may also use plugfones 102. NASCAR, NHRA, and team sport fans looking to reduce the noise of the race cars or game noise yet who want to listen to driving teams, commentators, or the like via a radio or other broadcast may also use plugfones 102. Everyday users may use plugfones 102 while operating lawnmowers, weed eaters, chainsaws, woodworking tools, vacuums, etc.

Although the foregoing description contains many specifics, these should not be construed as limiting the scope of the invention or of any of the appended claims, but merely as providing information pertinent to some specific embodiments that may fall within the scopes of the invention and the appended claims. Various embodiments are described, some of which incorporate differing features. The features illustrated or described relative to one embodiment are interchangeable and/or may be employed in combination with features of any other embodiment herein. In addition, other embodiments of the invention may also be devised which lie within the scopes of the invention and the appended claims. The scope of the invention is, therefore, indicated and limited only by the appended claims and their legal equivalents. All additions, deletions and modifications to the invention, as disclosed herein, that fall within the meaning and scopes of the claims are to be embraced by the claims.

What is claimed is:

1. A system, comprising:
   a first earplug adapted to fit within an ear canal of a user, the earplug comprising:
      an earplug body with a deformable exterior; and
      a channel passing longitudinally through the earplug with a first opening, a second opening, a plurality of grooves;
   a speaker;
   a housing maintaining the speaker, the housing comprising:
      a first portion for cupping a proximal end of the speaker; and
      a second portion comprising an elongated stem, wherein the stem is greater in length than the first portion, wherein the stem comprises a plurality of ridges configured to reversibly engage the channel, wherein the plurality of grooves complementary fit with the plurality of ridges, wherein the stem resides at least partially within the earplug body; and
   a wireless receiver for receiving audio data, wherein a wire extends from the wireless receiver to the speaker.

2. The system of claim 1, wherein the earplug is adapted to provide at least a twenty-five decibel decrease to external sounds.

3. The system of claim 1, wherein the earplug is adapted to receive the stem of the housing within the channel of the earplug.

4. The system of claim 3, wherein the stem comprises the plurality of ridges that frictionally engage the channel, wherein the channel comprises a deformable material that conforms to the stem.

5. The system of claim 1, wherein the earplug is deformable and the housing is substantially rigid.

6. The system recited in claim 1, wherein the earplug comprises a more rigid center and a more deformable exterior.

7. The system of claim 1, further comprising a second earplug configured substantially identically relative to the first earplug.

8. A system comprising:
- a first earplug adapted to fit within an ear canal of a user, the earplug comprising:
  - an earplug body with a deformable exterior comprising a first material; and
  - a channel passing longitudinally through the earplug with a first opening and a second opening with a plurality of grooves within the channel, the channel comprising a second material;
- a first speaker;
- a housing maintaining the speaker in the housing comprising:
  - a stem extending distally from a body of the housing, wherein the stem is greater in length than the body of the housing, wherein the stem comprises a plurality of circumferential ridges and is configured to reversibly and complimentary fit with the plurality of grooves within the channel of the first earplug, wherein the channel conforms to the stem.

9. The system of claim 8 comprising a wireless receiver for receiving audio data from an audio device.

10. The system of claim 9, wherein the wireless receiver comprises a first wire extending from at least one end of the wireless receiver to the speaker, wherein the wireless receiver is configured to received audio data and relay it to the first speaker.

11. The system of claim 8 further comprising a second earplug configured substantially identically relative to the first earplug.

12. The system of claim 10, wherein the wireless receiver comprises a second wire extending from the wireless receiver from an opposite end of the first wire, the second wire extending to a second speaker, wherein the wireless receiver is configured to receive the audio data and relay it to the second speaker.

13. The system of claim 8, wherein the earplug is adapted to provide at least a twenty-five decibel decrease to external sounds.

14. The system of claim 8, wherein the earplug is adapted to receive the stem of the housing within the channel of the earplug.

15. The system of claim 14, wherein the stem comprises a plurality of ridges that frictionally engage the channel.

16. The system of claim 15, wherein the earplug is interchangeable and reversibly fixed to the stem.

17. The system of claim 8, wherein the earplug is deformable and the housing is substantially rigid.

18. The audio system recited in claim 8, wherein the earplug comprises a more rigid center and a more deformable exterior.

* * * * *